United States Patent
Kwetkat et al.

[11] Patent Number: 5,977,404
[45] Date of Patent: Nov. 2, 1999

[54] AMPHIPHILIC COMPOUNDS WITH AT LEAST TWO HYDROPHILIC AND AT LEAST TWO HYDROPHOBIC GROUPS BASED ON DI-, OLIGO- AND POLYOL ETHERS

[75] Inventors: Klaus Kwetkat, Lünen; Wolfgang Schröder, Dorsten, both of Germany

[73] Assignee: Huels Aktiengesellschaft, Marl, Germany

[21] Appl. No.: 08/836,665

[22] PCT Filed: Sep. 15, 1995

[86] PCT No.: PCT/EP95/03634

§ 371 Date: Jun. 26, 1997

§ 102(e) Date: Jun. 26, 1997

[87] PCT Pub. No.: WO96/16033

PCT Pub. Date: May 30, 1996

[30] Foreign Application Priority Data

Nov. 21, 1994 [DE] Germany ............................ 44 41 363

[51] Int. Cl.$^6$ ...................................... C07F 11/00
[52] U.S. Cl. .................. 562/36; 562/8; 562/20; 568/626; 568/672; 568/673; 510/364; 510/418; 510/434
[58] Field of Search .................... 562/36, 8, 20; 568/626, 672, 667, 664, 678, 687, 308, 376, 382; 561/673; 510/364, 418, 434

[56] References Cited

U.S. PATENT DOCUMENTS 2,091,956  9/1937  Brenner .
5,160,450  11/1992  Okahara .

FOREIGN PATENT DOCUMENTS 3843327  6/1990  Germany .
60096695  10/1962  Japan .

OTHER PUBLICATIONS

CA:111:215073 abs of JP01063538, Mar. 1989.
CA:89:581507 abs of DE2803123, Aug. 1978.
CA:109:169821 abs of "A convenient systhesis of substituted poly ether diols", J Org Chem 53(21), pp. 5179–81, 1988.
"Alkanediyl–α,ω–bis(dimethylalkylammonium bromide) Surfactants. 1. Effect of the Spacer Chain Length on the Critical Micelle Concentration and Micelle Ionization Degreee", R. Zana, et al., Langmuir (1991), vol. 7, pp. 1072–1075.
"Dependence of Aggregate Morphology on Structure of Dimeric Surfactants", Nature, vol. 362, Mar. 18, 1993, R. Zana, et al.
"Alkanediyl–α,ω–bis(dimethylalkylammonium bromide) Surfactants. 3. Behavior at the Air–Water Interface" E. Alami, et al., Langmuir 1993, vol. 9, pp. 1465–1467, American Chemistry Society, 1993.

*Primary Examiner*—Gary Geist
*Assistant Examiner*—Jean F Vollano
*Attorney, Agent, or Firm*—Oblon, Spivak, McClelland, Maier & Neustadt, P.C.

[57] ABSTRACT

The invention relates to amphiphilic compounds of the general formula (I) with at least two hydrophilic and at least two hydrophobic groups based on di, oligo or polyethers. The amphiphilic compounds of this invention are highly surface active and are suitable as emulsifiers, demulsifiers, detergents, dispersants and hydrotropes for industrial and domestic purposes, e.g. in the fields of metalworking, ore separation, surface treatment, washing and cleaning, cosmetics, medicine and food processing and preparation.

8 Claims, No Drawings

AMPHIPHILIC COMPOUNDS WITH AT LEAST TWO HYDROPHILIC AND AT LEAST TWO HYDROPHOBIC GROUPS BASED ON DI-, OLIGO- AND POLYOL ETHERS

This is the national stage of PCT/EP 95/03634 filed Sep. 15, 1995.

BACKGROUND OF THE INVENTION

1. Field of the Invention

The invention relates to amphiphilic compounds with at least two hydrophilic and at least two hydrophobic groups based on di-, oligo- or polyol ethers.

2. Description of the Background

A wide variety of anionic, cationic, nonionic and zwitterionic compounds are known as amphiphilic substances. By far the most of these substances consist of a hydrophilic head group and at least one hydrophobic part.

With the amphiphilic substances there is a need, for ecological reasons, for example concerning the reduction in the cost of packaging and transport, to achieve an increasingly greater effect per mass of substance employed. Since optimization by mixing amphiphilic substances produces only very limited advances, novel amphiphilic substances with greater efficiency are required. It is therefore necessary in particular to find substances with lower critical micelle concentrations and/or lower surface and interfacial tensions in order to be able to reduce markedly the amounts of active substance employed.

Initial approaches to a solution in this direction by doubling one part of the structure (hydrophilic head group, hydrophobic group) have already been disclosed. Thus, cationic surface-active compounds can be obtained by adding long-chain alkyl halides onto permethylated alkylenediamines [R. Zana, M. Benrraou, R. Rueff, Langmuir, 7 (1991) 1072; R. Zana, Y. Talmon, Nature, 362 (1993) 228; E. Alami, G. Beinert, P. Marie, R. Zana, Langmuir, 9 (1993) 1465].

Anionic surface-active compounds with at least two hydrophobic and at least two hydrophobic groups have to date been prepared only on the basis of diglycidyl ethers (U.S. Pat. No. 5,160,450, JP 01 304 033, JP 4 124 165). However, diglycidyl ethers are regarded as toxicologically objectionable and are rather costly. Furthermore, epichlorohydrin is used for their preparation, which leads to large amounts of residues so that these compounds are no longer in accord with the times from the ecotoxicological and economic viewpoints.

SUMMARY OF THE INVENTION

The object therefore was to find amphiphilic compounds which have at least two hydrophilic and at least two hydrophobic groups, the amphiphilic compounds having a very high efficiency relative to the amount used, and which furthermore can be prepared from raw materials which are easily available industrially and without large amounts of unwanted by-products being formed.

The object is achieved according to the invention by amphiphilic di-, oligo- or polyethers whose basic skeletons can be prepared fr di-, oligo- or polyol ethers and α-epoxides. The corresponding di-, oligo- or polyethers can be alkoxylated and subsequently or directly converted into anionic amphiphilic compounds by, for example, reacting the abovementioned compounds with sulfur trioxide/inert gas, oleum, chlorosulfonic acid or sulfamic acid, with polyphosphoric acid, with a haloacetic acid, with a sultone, with a taurine or with maleic anhydride and sodium bisulfite and subsequently neutralizing in each case.

DETAILED DESCRIPTION OF THE INVENTION

The amphiphilic compounds according to the invention are therefore compounds of the general formula I

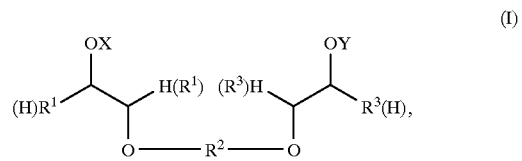

(I)

where $R^1$, $R^2$, $R^3$, X and Y in the formula I have the meanings described below, and where $R^1$ and $R^3$ each occur once in the formula I.

$R^1$ and $R^3$ are, independently of one another, an unbranched or branched, saturated or unsaturated hydrocarbon radical with 1 to 22, preferably 6 to 18, carbon atoms.

Specific substituents $R^1$ and $R^3$ which may be mentioned are the radicals methyl, ethyl, n-propyl, n-butyl, n-pentyl, n-hexyl, n-heptyl, n-octyl, n-nonyl, n-decyl, n-undecyl, n-dodecyl, n-triadecyl, n-tetradecyl, n-penta-decyl, n-hexadecyl, n-heptadecyl, n-octadecyl, n-nonadecyl, n-eicosyl, n-heneicosyl, n-docosyl and their branched-chain isomers, and the corresponding singly, doubly or triply unsaturated radicals.

$R^2$ is a spacer consisting of an unbranched or branched chain with 2 to 100 carbon atoms, which in each case contains 0 to 20 oxygen, 0 to 20 nitrogen, 0 to 4 sulfur and 0 to 3 phosphorus atoms, and which has 0 to 20 functional side groups such as, for example, hydroxyl, carbonyl, carboxyl, amino and/or acylamino groups.

The spacer $R^2$ is, in particular, as basic skeleton, unbranched or branched alkylene chains

(II)

with a=2 to 18, preferably a=2 to 6;

as basic skeleton, unbranched or branched alkenylene chains

(III)

with b+c=2 to 16, where b and c are each greater than zero;

as basic skeleton, unbranched or branched alkynylene chains

(IV)

with d+e=2 to 16, where d and e are each greater than zero, and where in the basic skeletons according to formulae II to IV the spacer contains at any desired point in the chain, independently of one another additionally 0 to 4 carbonyl, carboxyl, amino or acylamino groups;

alicycles according to the formula V

(V)

with f and g each independently of one another equal to 1 to 6 or according to formula VI −3(4), 8(9)-di(methylene)-trycyclo[5.2.1.0$^{2,6}$]decane-(VI);

unsubstituted or substituted aromatics according to the formula VII

$$—C_hH_{2h}—C_{10}R_6—C_jH_{2j}— \qquad (VII)$$

or according to the formula VIII

$$—C_hH_{2h}—C_{10}R_6—C_jH_{2j}— \qquad (VIII)$$

with h, j, $j_1$ and $j_2$ each independently of one another equal to 0 to 8 and i=1 to 8 and with R independently of one another in each case equal to H or $C_1$- to $C_6$-alkyl;

a chain with functional side groups, in particular hydroxyl, carbonyl, carboxyl, amino and/or acylamino groups.

Furthermore, the spacer $R_2$ in each case contains 0 to 20, preferably 1 to 12, oxygen and/or nitrogen atoms, 0 to 4 sulfur atoms and 0 to 3 phosphorus atoms, with at least one of the heteroatoms occurring at least once.

$R_2$ furthermore has, in particular, the meaning of a compound according to the formula IX

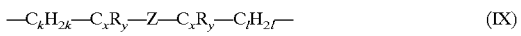
$$—C_kH_{2k}—C_xR_y—Z—C_xR_y—C_lH_{2l}— \qquad (IX)$$

with k and l each equal, independently of one another, to 0 to 8, x=6 and y=4 or x=10 and y=6 or x=14 and y=8, and z=O, CO, NH, N—$CH_2$—CH(OX)—$R^1$, $NR^1$, N—$C(O)R^1$, $SO_2$ or according to the formula IXa $$—CH_2—CH(OCH_2CH(OX)—R^1)—CH_2—\text{or an isomer} \qquad (IXa)$$

or 2,2'-methylenebis(1,3-dioxolane-5-methylene)- or acetals, especially diacetals of dialdehydes and di-, oligo- or polyols, where $R^1$ is a hydrocarbon radical with 1 to 22 carbon atoms, and X is a substituent which carries a functional group and has the meaning indicated hereinafter, of a compound according to the formula X

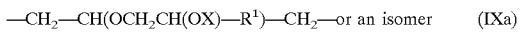
$$—C_mH_{2m}—(OC_nH_{2n})_p—C_qH_{2q}— \qquad (X)$$

with m=1 to 4, n=2 to 4, p=1 to 20, preferably p=1 to 4, and q=1 to 4, where mixed alkoxide units may also occur and then the sequence of the alkoxide units is arbitrary, of a compound according to the formula XI

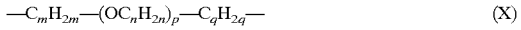
$$—C_rH_{2r}(RNC_sH_{2s})_t—C_uH_{2u}— \qquad (XI)$$

or according to the formula XII $$—[C_rH_{2r}[RN—C(O)—NR]_t—C_uH_{2u}]_w— \qquad (XII)$$

or according to the formula XIII $$—[C_rH_{2r}[RNC(O)C_vH_{2v}C(O)NR]_t—C_uH_{2u}]_w— \qquad (XIII)$$

or according to the formula XIV $$—[C_rH_{2r}[RN—C(O)—CH=CH—C(O)—NR]_t—C_uH_{2u}]_w— \qquad (XIV)$$

or according to the formula XV $$—[C_rH_{2r}[RNC(O)C_xR_yC(O)NR]_t—C_uH_{2u}]_w— \qquad (XV)$$

with r=2 to 4, s=2 to 4, t=1 to 20, preferably t=1 to 4, u=2 to 4, v=0 to 12, w=1 to 6, x=6 and y=4 or x=10 and y=0 or x=14 and y=8 with R independently of one another equal to H or $C_1$- to $C_6$-alkyl.

X and Y are, independently of one another, substituents of the formula XVI

$$—(C_2H_4O)\alpha(C_3H_6O)\beta H \qquad (XVI)$$

with $\alpha$=0 to 50, preferably $\alpha$=10 to 30, $\beta$=0 to 60, preferably $\beta$=20 to 40, and $\alpha+\beta$=1 to 100, preferably $\alpha+\beta$=10 to 50, and where the alkoxide units are incorporated randomly or blockwise and the sequence is arbitrary, or substituents of the formula XVII

$$—(C_2H_4O)_\gamma(C_3H_6O)_\delta—FR \qquad (XVII)$$

with in each case $\gamma$=0 to 20, preferably $\delta$=0 to 8, $\delta$=0 to 20, preferably $\delta$=0 to 12, and $\gamma+\delta$=0 to 40, preferably $\gamma+\delta$=5 to 20, where FR is a functional radical —$CH_2$—COOM, —$SO_3M$, —$P(O(OM))_2$, —$C_2H_4$—$SO_3M$ or —O—C(O)—$C_2H_3(SO_3M)$—$CO_2M'$ with M, M'=alkali metal, ammonium, alkanolammonium or ½ alkaline earth metal, or substituents of the formula XVIII

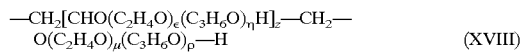
$$—CH_2[CHO(C_2H_4O)_\epsilon(C_3H_6O)_\eta H]_z—CH_2—O(C_2H_4O)_\mu(C_3H_6O)_\rho—H \qquad (XVIII)$$

with z=3 to 6, preferably z=4 and $\epsilon$ to $\mu$=0 to 30, preferably $\epsilon$ or $\mu$=0 to 10, and $\eta$ or $\rho$=0 to 30, preferably $\eta$ or $\rho$=0 to 10, and where the alkoxide units are likewise incorporated randomly or blockwise and the sequence is arbitrary.

The degree of alkoxylation is in each case an average and can assume any desired, including non-integral, value within the stated limits.

The amphiphilic compounds according to the invention are usually distinguished by extremely low critical micelle concentrations (CMC) and very low surface and interfacial tensions (for example in the presence of paraffin), which must be ascribed to their special structure—at least two hydrophilic groups and at least two hydrophobic groups. Furthermore, most of them display a rather high hydrophilic suspension capacity which is about halfway between that of conventional surfactants and that of pentasodium tripolyphosphate. Some of these compounds are extremely rapid wetting agents.

The amphiphilic compounds according to this invention are particularly suitable as emulsifiers, demulsifiers, detergents, dispersants and hydrotropes in industry and domestically, for example in the areas of metal processing, ore production, surface treatment, washing and cleaning, cosmetics, medicine and foodstuff processing and preparation.

In these cases they can be combined with all customary anionic, nonionic, cationic and ampholytic surface-active substances. Examples of nonionic surface-active substances which can be used for a combination and which may be mentioned are: fatty acid glycerides, fatty acid polyglycerides, fatty acid esters, ethoxylates of higher alcohols, polyoxyethylene fatty acid glycerides, polyoxyethylene/propylene glycol fatty acid esters, polyoxyethylene sorbitan fatty acid esters, polyoxyethylene castor oil or hardened castor oil derivatives, polyoxyethylene lanolin derivatives, polyoxyethylene fatty acid amides, polyoxyethylene alkylamines, alkanolamines, alkylamine oxides, derivatives of protein hydrolysates, hydroxy-mixed ethers, alkyl polyglycosides and alkylglucamides.

Examples of anionic surface-active substances which can be used for combinations and which may be mentioned are: soaps, ether carboxylic acids and salts thereof, alkylsulfonates, α-olefinsulfonates, sulfonates of higher fatty acid esters, higher alcohol sulfates, alcohol ether sulfates, hydroxy-mixed ether sulfates, salts of phosphate esters, taurides, isethionates, linear alkylbenzenesulfonates, cumenesulfonate, alkylarylsulfonates, sulfates of polyoxyethylene fatty acid amides and salts of acylamino acids.

Examples of customary cationic surface-active substances which can be used for combinations and which may be mentioned are: alkyltrimethylammonium salts, dialkyl- dimethylammonium salts, alkyldimethylbenzylammonium salts, alkylpyridinium salts, alkylisquinoinium salts, benzethonium chlorides and cationic acylamino acid derivatives.

Examples of ampholytic surface-active substances which can be used for combinations and which may be mentioned are: amino acids, betaines, sulfobetaines, imidazoline derivatives, soybean oil lipids and lecithin.

Furthermore, the amphiphilic compounds according to the invention can also be combined together on their own.

It is likewise possible to add conventional additives to the amphiphilic compounds according to the invention. Such additives are specifically selected for a formulation and normally comprise inorganic salts such as sodium chloride and sulfate, and builders, hydrotropes, UV absorbers, softening agents, chelating agents, viscosity modifiers and fragrances.

The abovementioned compounds can be prepared from di-, oligo- or polyols and at least twice the number of equivalents of α-epoxides in the presence of a catalyst. In this connection, the catalyst can originate from the group of basic or acidic substances such as alkali metal alcoholates, aluminosilicates, sheet silicates, aluminum oxides, boron trifluoride etherate, aluminum chloride, niobic acid, HY zeolite and alkali metals. The reaction does not take place with complete selectivity for opening of the epoxide from the unsubstituted sides so that mixtures of primary and secondary di-, oligo- or polyols are formed as intermediates. The products, which are liquids or soften at low temperaturs, or their alkoxylates can subsequently be reacted with sulfurtrioxide/inert gas, oleum, chlorosulfonic acid or sulfamic acid, with polyphosphoric acid, with a haloacetic acid, with a sultone with a taurine or with maleic anhydride and sodium bisulfite and neutralized with aqueous alkali metal or alkaline earth metal hydroxides or aqueous ammonia or alkanolamines. If required, the products are bleached in aqueous solution with hydrogen peroxide (0.1 to 2.0% based on solid).

EXAMPLES

The following examples are intended to explain the invention but not restrict it thereto.

EXAMPLE 1

$R^1 = R^3 = C_6H_{13}$ $R^2 = C_2H_4$ $X = Y = SO_3Na$. 53.1 g or ethylene glycol and 1.0% by weight (based on epoxide) of sodium methanolate are introduced into a 250 ml three-necked flask with stirrer, thermometer, protective gas connector and reflux condenser, the mixture is heated until stirrable, and 229.8 g of 1,2-epoxyoctane are added. The reaction mixture is then heated to 180° C., and the reaction is stopped after 6 hours (epoxide completely reacted according to GC). It is washed with sodium bicarbonate solution, and the mixture of product isomers is distilled at 130 to 145° C. (0.1 mbar). Yield: 149.4 g (80%), purity according to GC>95%.
Sulfation 49.6 g of the diol obtained above are added dropwise to a mixture of 61.3 g of chlorosulfonic acid and 31.8 g of acetic acid in 200 ml of dichloro-methane in such a way that the temperature does not exceed 5° C. The mixture is then stirred at room temperature for 3 hours (the diol mixture has completely reacted according to a check by thin-layer chromatography). It is neutralized with 2 normal sodium carbonate solution and diluted with saturated sodium bicarbonate solution. The product is extracted with n-butanol, and then the alcohol is removed. The purity is checked by thin-layer chromatography and NMR. Yield: 70.3 g (80% of theory), purity: 90% (mixture of isomers).
Characteristic $^{13}$C-NMR data (DMSO-D$_6$):

76.3 ppm, 72.1 ppm, 73.0 ppm, 71.6 ppm, 69.9 ppm, 69.4 ppm, 30.6 ppm, 28.6 ppm, 28.4 ppm, 25.0 ppm, 21.4 ppm, 20.3 ppm, 20.2 ppm, 13.3 ppm. CMC (in deionized water, 20° C.) 5.5 g/l; $\gamma_{CMC}$: 30.5 mN/m (deionized water, 20° C.).

EXAMPLE 2

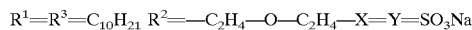
$R^1 = R^3 = C_{10}H_{21}$ $R^2 = -C_2H_4-O-C_2H_4-$ $X = Y = SO_3Na$ 21.4 g of diethylene glycol and 3.0% by weight (based on epoxide) of Al$_2$O$_3$ are introduced into a 250 ml three-necked flask with stirrer, thermometer, protective gas connection and reflux condenser, the mixture is heated until stirrable, and 82.4 g of 1,2-epoxydodecane are added. The reaction mixture is then heated to 180° C. and the reaction is stopped after 8 hours (epoxide completely reacted according to GC). It is washed with sodium bicarbonate solution. Yield: 61.9 g (52%), purity according to GC>95%, isomer ratio: secondary diol to primary diol (R' and OX, and R$^2$ and OY partly confused): 80:20.
Sulfation 49.6 g of the diol obtained above in 200 ml of dichloromethane are added dropwise to a mixture of 47.1 g of chlorosulfonic acid and 24.1 g of acetic acid in such a way that the temperature does not exceed 5° C. The mixture is then stirred at room temperature for 3 hours (the diol mixture has completely reacted according to a check by thin-layer chromatography). It is neutralized with 2 normal sodium carbonate solution and diluted with saturated sodium bicarbonate solution. The product is extracted with n-butanol, and then the alcohol is removed. The purity is checked by thin-layer chromatography and NMR. Yield:56.7 g (80% of theory), purity: 90% (mixture of isomers), characteristic $^{13}$C-NMR data (DMSO-D$_6$): 80.7 ppm, 80.3 ppm, 73.7 ppm, 72.5 ppm, 72.3 ppm, 72.1 ppm, 71.1 ppm, 69.8 ppm, (both isomers), 34. ppm, 33.5 ppm, 32.0 ppm, 31.8 ppm, 31.6 ppm, 24.8 ppm, 16.0 ppm.

CMC (in deionized water, 20° C.): 0.2 g/l, $\gamma_{CMC}$: 33.0 mN/m (deionized water, 20° C.), $\gamma_{paraffin}$: 2.5 mN/m (drinking water, 20° C., 0.1 g/l active substance).

EXAMPLE 3

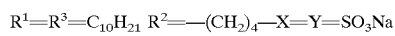
$R^1 = R^3 = C_{10}H_{21}$ $R^2 = -(CH_2)_4-$ $X = Y = SO_3Na$ 18.1 g of 1,4-butanediol and 3.0% by weight (based on epoxide) of Al$_2$O$_3$ are introduced into a 250 ml three-necked flask with stirrer, thermometer, protective gas connection and reflux condenser, the mixture is heated until stirrable, and 83.9 g of 1,2-epoxydodecane are added. The reaction mixture is then heated to 180° C., and the reaction is stopped after 10 hours (epoxide completely reacted according to GC). It is washed with sodium bicarbonate solution. Yield:70.6 g (50%), purity according to GC>95%, isomer ratio: secondary diol to primary idol: 90:10.
Sulfation 62.2 g of the diol obtained above in 200 ml of dichloromethane are added dropwise to a mixture of 38.8. g of chlorosulfonic acid and 19.9 g of acetic acid in such a way that the temperature does not exceed 5° C. The mixture is then stirred at room temperature for 3 hours (the idol mixture has completely reacted according to a check by thin-layer chromatography). It is neutralized with 2 normal sodium carbonate solution and diluted with saturated sodium bicarbonate solution. The product is extracted with n-butanol, and then the alcohol is removed. The purity is checked by thin-layer chromatography and NMR. Yield: 39.9 g (60% of theory), purity: 90% (mixture of isomers), characteristic $^{13}$C-NMR data (DMSO-D$_6$): 78.2 ppm, 74.6 ppm, 74.2 ppm, 72.0 ppm, 69.8 ppm, (broad), 67.3 ppm, (both isomers), 30.8 ppm, 28.5 ppm, 28.2 ppm, 21.5 ppm, 13.1 ppm.

CMC (in deionized water, 20° C.): 0.0058 g/l, $\gamma_{CMC}$: 30.0 mN/m (drinking water, 20° C.), $\gamma_{paraffin}$: 2.0 mN/m (drinking water, 20° C., 0.1 g/l active substance).

We claim:

1. Amphiphilic compounds of the general formula I

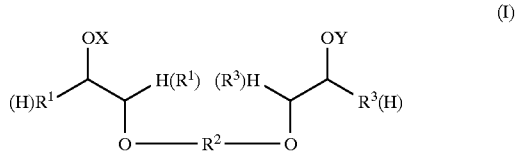

(I)

in which $R^1$ and $R^3$ are, independently of one another, a hydrocarbon radical with 6 to 22 carbon atoms with the proviso that each of $R^1$ and $R^3$ occurs only once in the formula, $R^2$ is selected from the group consisting of an alkylene chain of the formula —$C_aH_{2a}$—wherein a is 2 to 18, an alkenylene chain of the formula —$C_bH_{2b}$—CH=CH—$C_cH_{2c}$—where b and c are each greater than 0 and b+c=2 to 16, an alkynylene chain of the formula —$C_dH_{2d}$—C≡C—$C_eH_{2e}$—where d and e are each greater than 0 and d+e=2 to 16, an alicycle of the formula —$C_fH_{2f}$—cyclo $C_6H_{10}$—$C_gH_{2g}$—where f and g each equal 1 to 6, -3(4), 8(9)—di (methylene)—tricyclo [5.2.1.0$^{2.6}$] decane, an aromatic of the formula $C_hH_{2h}$—$C_6R_4$—$C_iH_{2i}$—$C_6R_4)_{j1}$—$C_{j2}H_{2j2}$ and an aromatic of the formula $C_hH_{2h}$—$C_{10}R_6$—$C_jH_{2j}$—where h, j$_1$ and j$_2$ each equal to 0 to 8 and i equals 1 to 8 with each R being H or C$_{1-6}$ alkyl; and X and Y are each selected from the group consisting of substituents of the formula —(C$_2$H$_4$O)$_\alpha$(C$_3$H$_6$O)$_\beta$H where $\alpha$ is 0 to 50 and $\beta$ is 0 to 60 and $\alpha+\beta$=1 to 100, the formula —(C$_2$H$_4$O)$_\gamma$(C$_3$H$_6$O)$_\delta$—FR where $\gamma$ and $\delta$ each equals 0 to 20, $\gamma+\delta$=0 to 40 and FR is selected from —CH$_2$—COOM or —SO$_3$M or P(O) (OM)$_2$ or C$_2$H$_4$SO$_3$M or —O—C(O)—C$_2$H$_3$ (SO$_3$M)—CO$_2$M$^1$ where M and M$^1$ are each alkali metal or ammonium or alkanolanmmonium or ½ alkaline earth metal, the formula CH$_2$[CHO(C$_2$H$_4$O)$_\epsilon$(C$_3$H$_6$O)$_\eta$H]$_z$—CH$_2$—O (C$_2$H$_4$O)$_{s2}$ (C$_3$H$_6$O)$_\rho$-H where z is 3 to 6, $\epsilon$ and $\mu$ each equals 0 to 30, $\eta$ and $\rho$ each equals 0 to 30 and wherein any alkoxide units present are incorporated randomly or block-wise and the sequence is arbitrary.

2. Amphiphilic compounds according to claim 1, wherein the hydrocarbon radicals $R^1$ and $R^3$ are unbranched or branched, saturated or unsaturated.

3. Amphiphilic compounds according to claim 1, characterized in that the hydrocarbon radicals $R^1$ and $R^3$ in the formula I contain, independently of one another, 6 to 18 carbon atoms.

4. Amphiphilic compounds according to claim 1, characterized in that $R^2$ has at least one substituent selected from the group consisting of hydroxyl, carbonyl, carboxyl, amino and acylamino.

5. Amphiphilic compounds according to claim 1 characterized in that compounds selected from the group consisting of alkali metal alcoholates, sheet silicates, aluminosilicates, aluminum oxides and niobic acid are used as catalysts to prepare the compounds by the reaction of di-, oliogo- or polyols and monepoxides.

6. A method of cleaning a hard surface, comprising contacting the hard surface with the amphiphilic compounds according to claim 1.

7. The amphiphilic compounds of claim 1, wherein:

$R^1$ and $R^3$ are C$_{10}$H$_{21}$ groups;

$R^2$ is —C$_4$H$_8$—; and

X and Y are SO$_3$Na.

8. A method of claiming a hard surface, comprising contacting the hard surface with the amphiphilic compound according to claim 7.

* * * * *

UNITED STATES PATENT AND TRADEMARK OFFICE
CERTIFICATE OF CORRECTION

PATENT NO. : 5,977,404
DATED : November 2, 1999
INVENTOR(S) : Klaus Kwetkat et al.

It is certified that error appears in the above-identified patent and that said Letters Patent is hereby corrected as shown below:

Column 1,
Line 41, "hydrophobic" should read -- hydrophilic --;
Line 62, "fr" should read -- from --.

Column 2,
Line 24, "1" should read -- 6 --;
Line 28, "n-triadecyl," should read -- n-tridecyl, --.

Column 3,
Line 3, "—$C_hH_{2h}$—$C_{10}R_6$—$C_jH_{2j}$—" should read -- —$C_hH_{2h}$—$C_6R_4$—$(C_iH_{2i}$—$C_6R_4)_{j1}$—$C_{j2}H_{2j2}$— --;

Line 10, "i = 1 to 8" should read -- i = 0 to 8 --;
Lines 15 and 19, "$R_2$" should read -- $R^2$ --;
Line 41, "q = 1 to 4," should read -- q = 0 to 4, --;
Line 61, "y = 0" should read -- y = 6 --.

Column 4,
Line 9, "$\delta$ = 0 to 8," should read -- $\gamma$ = 0 to 8, --;
Line 10, "y + $\delta$ = 0 to 40," should read -- y + $\delta$ = 1 to 40, --;
Line 20, "$\epsilon$ to" should read -- $\epsilon$ or --.

Column 5,
Line 5, "alkylisquinoinium" should read -- alkylisoquinolinium --.

Column 6,
Line 42, "34." should read -- 34.1 --;
Line 67, "idol" should read -- diol --

Column 7,
Line 36, "$C_hH_{2h}$—$C_6R_4$—$C_iH_{2i}$—" should read -- $C_hH_{2n}$—$C_6R_y$ -- $(C_iH_{2i}$- --;
Line 37, "$C_{j2}H_{2j2}$" should read -- $C_{j2}H_{j2}$ --.

Page 1 of 2

UNITED STATES PATENT AND TRADEMARK OFFICE
CERTIFICATE OF CORRECTION

PATENT NO.    : 5,977,404
DATED         : November 2, 1999
INVENTOR(S)   : Klaus Kwetkat et al.

It is certified that error appears in the above-identified patent and that said Letters Patent is hereby corrected as shown below:

<u>Column 8,</u>
Line 5, "$M^1$" should read -- $M'$ -- (both occurences);
Line 8, "$(C_2H_4O)_{82}$" should read -- $(C_2H_4O)_\mu$ --;
Line 37, "claiming" should read -- cleaning --.

Signed and Sealed this

Second Day of October, 2001

Attest:

NICHOLAS P. GODICI
*Attesting Officer*      *Acting Director of the United States Patent and Trademark Office*